United States Patent [19]

Shirato et al.

[11] Patent Number: 4,651,087
[45] Date of Patent: Mar. 17, 1987

[54] APPARATUS FOR MEASURING IMPURITIES IN ULTRAPURE WATER

[75] Inventors: Kozo Shirato, Omiya; Kazuyasu Kawashima, Yokohama; Yoshihiro Sato, Nagaoka, all of Japan

[73] Assignee: Erma Optical Works, Ltd., Tokyo, Japan

[21] Appl. No.: 583,355

[22] Filed: Feb. 24, 1984

[30] Foreign Application Priority Data

Jun. 28, 1983 [JP]  Japan .................................. 58-117841

[51] Int. Cl.$^4$ ........................................... G01N 27/00
[52] U.S. Cl. ................................ 324/71.4; 324/71.1
[58] Field of Search ............... 324/71.4, 71.1, 450, 324/438, 439, 446, 447, 448, 449; 377/12; 55/154

[56] References Cited

U.S. PATENT DOCUMENTS

| 3,921,006 | 11/1975 | Pontigny | 324/71.4 |
| 4,268,279 | 5/1981 | Shindo et al. | 55/16 |
| 4,434,647 | 3/1984 | Whitcomb et al. | 356/243 |

FOREIGN PATENT DOCUMENTS 2907188  8/1979  Fed. Rep. of Germany ........ 55/159

Primary Examiner—Michael J. Tokar
Attorney, Agent, or Firm—Watson, Cole, Grindle & Watson

[57] ABSTRACT

An electrical pulse apparatus for measuring impurities in ultrapure water includes a deaeration device connected to the conduit line supplying electrolyte to the hollow detector so as to deaerate the electrolyte and enable bubbles formed by electrolysis at the electrodes to be readily redissolved and thus increase measurement sensitivity and speed.

3 Claims, 3 Drawing Figures

APPARATUS FOR MEASURING IMPURITIES IN ULTRAPURE WATER

BACKGROUND OF THE INVENTION

1. Field of the Invention

The present invention relates to an apparatus for measuring the number or sizes of micro impurities such as fine dust or bacteria floating in ultrapure water.

2. Description of the Prior Art

Ultrapure water is water which has a specific resistivity of 16 MΩ·cm (25° C.) and contains impurities such as fine particles, organic materials, inorganic materials or bacteria only in units of ppb (1/1,000 of the ppm). Ultrapure water is indispensable to the manufacture of IC semiconductors. In particular, since the pattern size of current LSIs is as small as 1 μm, ultrapure water must not contain micro impurities having a size of 0.1 μm or more.

Methods of measuring micro impurities (to be referred to as impurities for brevity hereinafter) floating in ultrapure water currently include the light-blocking method, the light-scattering method, the laser-scattering method, the filter method, and the electrical pulse method.

Of these methods, the light-blocking method, the light-scattering method, and the laser-scattering method which utilize light provide only a low precision and cannot measure or detect impurities having a size of 0.5 μm or less or transparent impurities such as dead bacteria. Although the filter method which measures the impurities trapped by a microscope allows measurement of impurities having a size of 0.1 μm or less, sampling and measurement procedures require much labor and time.

In the electrical pulse method, a change in resistance which is obtained when an impurity passes through a small hole in a detector is obtained as a voltage pulse. The electrical pulse method theoretically allows measurement of impurities having a size of 0.1 μm or less and allows easy sampling and measurement. However, it sometimes happens that the electrolyte or ultrapure water causes electrolysis between the electrodes, bubbles become attached to the surfaces of the electrodes, and the detection sensitivity is signifcantly degraded. When a high current is flowed to improve detection sensitivity, electrolysis becomes more vigorous to present danger. Furthermore, since the interior of a detector is kept at a reduced pressure to draw by suction ultrapure water through the small hole in the detector, dissolved gases in the electrolyte in the detector or a manometer appear in the form of bubbles and adversely affect the operation of the manometer.

SUMMARY OF THE INVENTION

The present invention has been made in consideration of the drawbacks of the conventional methods and has for its object to provide an apparatus for measuring impurities in ultrapure water, which is improved over the electrical pulse method for a high detection sensitivity and high precision and which does not operate erratically.

In order to achieve this object, according to the present invention, a deaerating device having a tube disposed in a reduced pressure tank and consisting of a synthetic resin for allowing passage of only gases therethrough and preventing passage of liquids therethrough is placed in a path for supplying an electrolyte to a detector, and the electrolyte is flowed through the tube of the deaerating device.

An embodiment of the present invention will now be described with reference to the accompanying drawings.

DETAILED DESCRIPTION OF THE PREFERRED EMBODIMENT

Figure 1:
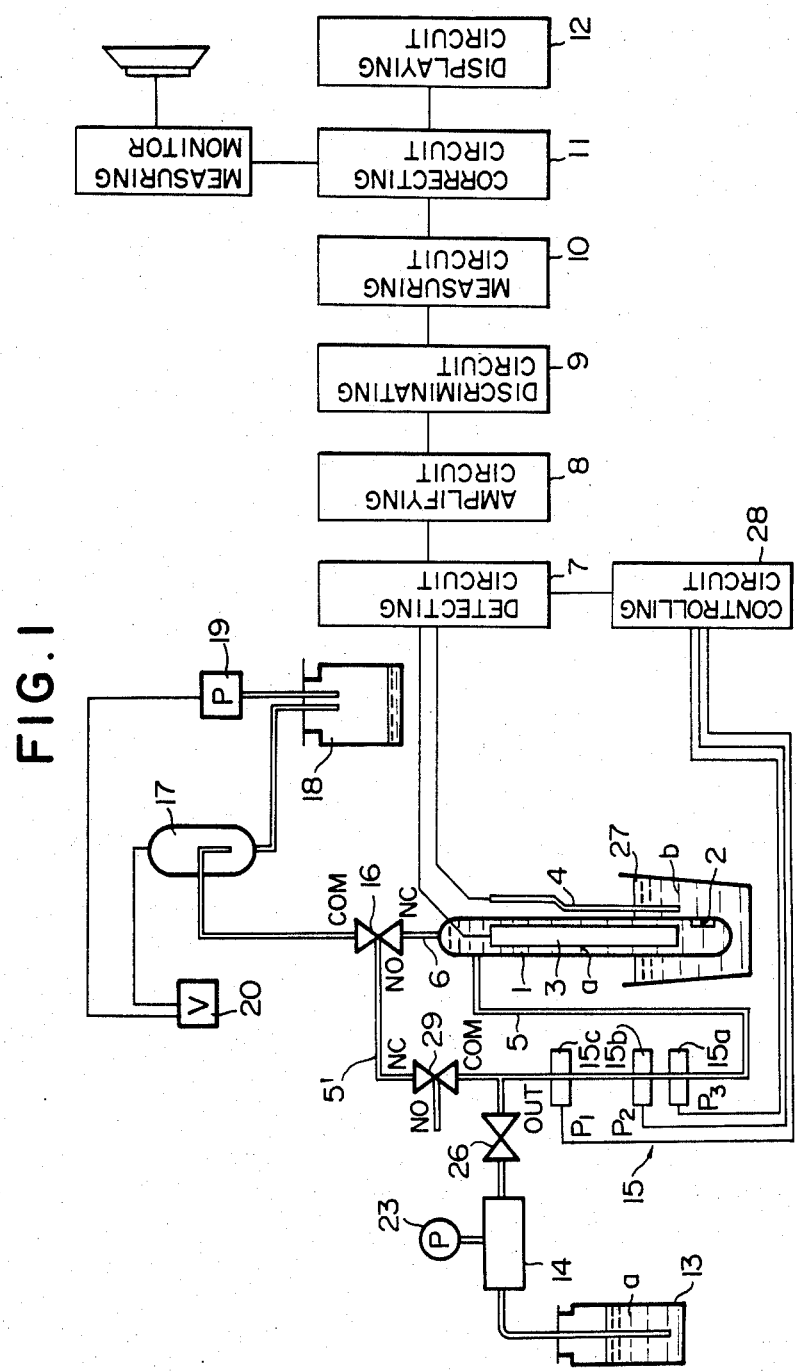
FIG. 1 is a view showing an embodiment of a measuring apparatus of the present invention.

A detector 1 has a hollow shape and consists of an electrical insulator such as glass. A small hole 2 is formed in the lower portion of the side wall of the detector to communicate the interior and exterior of the detector 1. An internal electrode (positive electrode) 3 is placed in the detector 1, while an external electrode (negative electrode) 4 is placed outside the detector 1. An electrolyte supply tube 5 and an exhaust tube 6 are connected to the detector 1.

The small hole 2 is formed in the lower portion of the side wall of the detector 1 such that a chip of a ruby or sapphire with the small hole 2 therein is fitted in the side wall of the detector 1. The small hole 2 has a small size (e.g., 10 μm diameter) so as not to allow simultaneous passage or more than one impurity.

As noted above, the internal electrode 3 and the external electrode 4 are arranged inside and outside the detector 1. A constant DC current is caused to flow between the electrodes 3 and 4, which are connected to pulse-detecting circuit 7. The detecting circuit 7 is connected in series with an amplifying circuit 8 for amplifying voltage pulses having a small amplitude, a discriminating circuit 9 for discriminating and shaping the amplified voltage pulses, a measuring circuit 10 for counting the voltage pulses, a correcting circuit 11 for correcting errors in the count of the voltage pulses, and a displaying circuit 12 for digitally displaying the number of impurities thus measured.

The electrolyte supply tube 5 supplies elctrolyte a from a water supply bottle 13 to the interior of the detector 1. A deaerating device 14 is disposed at the part of the path of the tube 5 which is at the side of the water supply bottle 13. A manometer 15 for measuring the liquid level by means of a photosensor is disposed at the part of the path of the tube 5 which is at the side of the detector 1. A branch tube 5' is connected between the deaerating device 14 and the manometer 15. The branch tube 5' is connected to the exhasut tube 6 of the detector 1 through a three-way electromagnetic valve 16. A glass tank 17 communicates with an exhaust bottle 18 and a vacuum pump 19 is connected to the exhaust bottle 18. Reference numeral 20 denotes a pressure sensor for maintaning the interior of the exhaust bottle at a given negative pressure.

Figure 2:
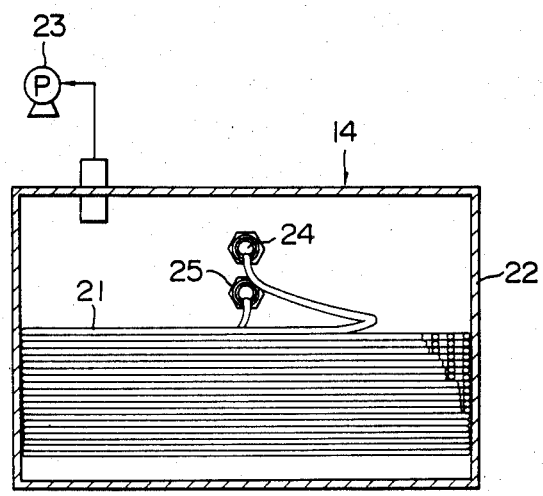
FIG. 2 is a sectional view showing an embodiment of a deaerating device to be used in the measuring apparatus of the present invention.
Figure 3:
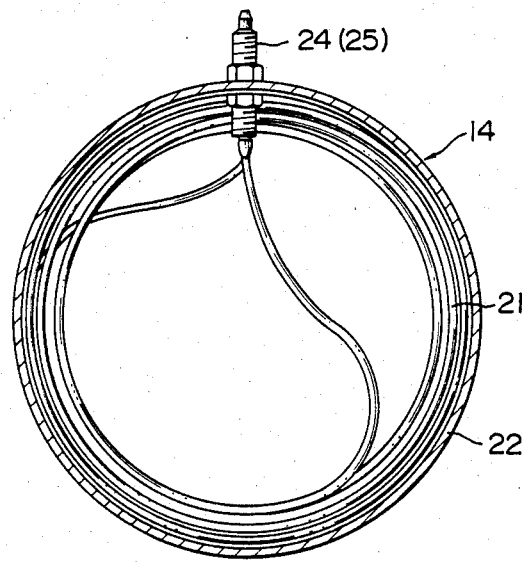
FIG. 3 is a cross-sectional view of the deaerating device shown in FIG. 2.

The deaerating device 14 deaerates dissolved gases in the electrolyte a contained in the water supply bottle 13 and supplies the deaerated electrolyte a to the detector 1. As shown in FIGS. 2 and 3, the deaerating device 14 comprises a tube 21 for flowing the electrolyte a therethrough, and a reduced pressure tank 22 housing the tube 21 therein and communicating with a vacuum pump 23.

The tube 21 consists of a synthetic resin material which passes gases only and does not pass liquids, such as an ethylene tetrafluoride resin material or silicone resin material. The inner diameter, wall thickness and/or length of the tube 21 vary in accordance with the material used. According to an experiment conducted, when the inner diameter of the tube 21 was 1.0 to 2.0 mm, the wall thickness was 0.2 to 0.5 mm, the length was 10 to 20 m, and the flow rate of the electrolyte which is to be deaerated was 10 to 25 ml/min, deaeration could be performed substantially completely. The tube 21 is housed in the reduced pressure tank 22 in a wound form without forming bends or twists.

The reduced pressure tank 22 is formed into a sealed box shape using a synthetic resin material or a metallic material and is connected to the vacuum pump 23 to be evacuated thereby. One end of the tube 21 in the wound form is connected to an inlet port connector 24, while the other end thereof is connected to an output port connector 25. The reduced pressure tank 22 is connected through the connectors 24 and 25 to the path for supplying the electrolyte a from the water supply bottle 13 to the detector 1, that is, an intermediate portion of the electrolyte supply tube 5. While the electrolyte a to be deaerated is flowed through the tube 21, the dissolved gases are deaerated from the electrolyte a and the deaerated electrolyte is supplied to the interior of the detector 1.

The mode of operation of the apparatus according to the present invention will now be described.

The electrolyte a contained in the water supply bottle 13 is supplied to the liquid circuit. When a water supply switch (not shown) is depressed (ON), a valve (to be referred to as an A-valve hereinafter) 26 for opening/closing between the deaerating device 14 and the electrolyte supply tube 5 is opened, and NC and COM sides of the three-way electromagnetic valve (to be referred to as a B valve hereinafter) 16 for opening/closing the branch tube 5' of the electrolyte supply tube 5, the exhaust tube 6 and the glass tank 17 are opened. By the suction force of the vacuum pump 19, the electrolyte a in the water supply bottle 13 is supplied to the deaerating device 14 and is deaerated through the tube 21. The deaerated electrolyte is supplied to the interior of the detector through the A-valve 26 and the manometer 15. The deaerated electrolyte inside the detector 1 is flowed to the glass tank 17 through the exhaust tube 6 and the B-valve 16 and is then exhausted into the exhaust bottle 18. Then, the overall liquid circuit is filled with the deaerated electrolyte a.

Subsequently, the A-valve 26 is closed, and a reagent bottle 27 holding ultrapure water b to be measured therein is placed below the detector 1. The small hole 2 of the detector 1 is immersed into the ultrapure water b to be measured, and a current is flowed between the internal and external electrodes 3 and 4 through the electrolyte a and the ultrapure water b. Measurement is thus started. The electrolyte is mixed with the ultrapure water b for providing a good conductivity.

When a measurement start switch (not shown) is depressed (ON), the A-valve 26 is closed, and the NC and the COM sides of the B valve 16 are opened. At the same time, the NO and COM sides of a three-way electromagnetic valve (to be referred to as a C-valve hereinafter) 29 interposed between the A-valve 26 and the B-valve 16 are opened. Then, the electrolyte in the liquid circuit is drawn from the exhaust tube 6 of the detector 1 to the exhaust bottle 18 through the glass tank 17 by means of the suction force of the vacuum pump 19. At the same time, air is introduced into the liquid circuit from the NO side of the C valve 29, and the liquid level in the manometer 15 is lowered to level $P_3$ through level $P_1$. When the liquid level of the manometer 15 reaches level $P_3$, a photosensor 15a is turned on. Upon turning on of the photosensor 15a, the NC side of the B-valve 16 is closed and the NO and COM sides thereof are opened. At the same time, the NO side of the C-valve 29 is closed and the COM and NC sides thereof are opened, and the liquid level of the manometer 15 begins to rise by the suction force of the vacuum pump 19. Since the interior of the detector 1 is kept at a negative pressure, the ultrapure water b in the reagent bottle 27 is drawn into the detector 1 through the small hole 2. When the liquid level of the manometer 15 reaches level $P_2$, a photosensor 15b is turned on. The detecting circuit 7 and so on are operated through a controlling circuit 28 to start measurement. When the ultrapure water b in the reagent bottle 27 is drawn into the detector 1 through the small hole 2, impurities in the ultrapure water b are also drawn. When an impurity passes through the small hole 2 of the detector 1, a resistance between the internal and external electrodes 3 and 4 is instantaneously increased, and an electrical pulse having an amplitude proportional to the size of the passed impurity is generated. The pulse is then detected by the detecting circuit 7 and is processed by the amplifying circuit 8, the discriminating circuit 9, the measuring circuit 10, and the correcting circuit 11. The number of impurities is digitally displayed at the displaying circuit 12.

When the liquid level in the manometer 15 reaches level $P_1$ a photosensor 15c is turned on and the measurement is terminated. While the liquid level in the manometer 15 rises from level $P_2$ to level $P_1$, the amount of the ultrapure water drawn into the detector 1 through the small hole 2 reaches the unit suction amount. Thus, the number of impurities contained in the unit suction amount of ultrapure water b is thus counted.

Since the apparatus of the present invention has the construction as described above, it provides the following effects:

(1) The apparatus of the invention allows easy sampling and measurement as in the case of the conventional electrical pulse method. The apparatus allows quick measurement of the number and size of impurities contained in ultrapure water with ease.

(2) When the size (diameter) of the small hole in the detector is properly selected, theoretically measurement of impurities having a size of 0.1 m$\mu$ or less can be performed. An actual apparatus allowed measurement of impurities having a size of 0.1 m$\mu$.

(3) Although slight electrolysis is caused between the internal and external electrodes during measurement, the electrolyte in the detector is sufficently deaerated so that bubbles formed upon electrolysis are easily dissolved in the electrolyte and may not become attached on the surfaces of the electrodes. Since bubbles are not attached to the surfaces of the electrodes, a current easily flows and only a small current need be flowed during the measuring operation. For this reason, electrolysis between the internal and external electrodes is hard to occur, and attachment of bubbles on the electrodes is prevented. Since a constant current flows between the internal and external electrodes, measurement reproducibility is good and high detection sensitivity is obtained.

(4) In the conventional methods, when the measurement time is prolonged, bubbles are attached on the surfaces of the electrodes and the detection sensitivity is degraded as time elapses. Accordingly, the unit suction amount of ultrapure water is small (0.1 ml) and measurement error is large. However, in the apparatus of the present invention, the unit suction amount of ultrapure water can be increased (0.25 to 0.5 ml) and measurements free from errors can be obtained.

(5) In the conventional methods, after each measurement, bubbles formed on the surfaces of the electrodes must be washed away, resulting in much labor and loss of electrolyte. The apparatus of the invention does not require such a procedure.

(6) In the conventional methods, when a liquid circuit is kept at a negative pressure by a vacuum pump for drawing ultrapure water through a small hole of a detector, dissolved gases in the electrolyte form bubbles which are introduced in the manometer during measurement, thus causing erratic operation. However, in the apparatus of the invention, the electrolyte in the liquid circuit is deaerated substantially completely. Accordingly, even if the liquid circuit is reduced in pressure to a pressure of 560 Torr by a vacuum pump, bubbles are not formed. Thus, the manometer may not operate erratically, and the liquid circuit can be kept at a high negative pressure to draw ultrapure water into the detector through the small hole within a short period of time. Measurement time can thus be reduced to the minimum.

(7) Since the measurement time is shortened, the portion of the electrolyte which is subjected to electrolysis is reduced. The effects of items (3) and (4) are further enhanced.

(8) The deaerated electrolyte from the deaerating device can be supplied to the detector and the liquid circuit on the on-line basis. Operability of the apparatus is thus improved.

(9) The deaerating device is compact in size and can be easily assembled in the measuring apparatus. Thus, the object of the present invention can be achieved.

It is further understood by those skilled in the art that the foregoing description is that of preferred embodiments of the disclosed apparatus for measuring impurities in ultrapure water and that various changes and modifications may be made in the invention without departing from the spirit and scope thereof.

We claim:

1. In an electrical pulse apparatus for measuring impurities in ultrapure water which includes
    a container for the ultrapure water whose impurities are to be measured,
    a hollow detector which has a portion extending into said container so as to be surrounded by said ultrapure water, said portion of said hollow detector having a small hole therein to enable ultrapure water in said container to pass into said hollow detector,
    a supply tank for a liquid electrolyte,
    a first conduit system connected between said supply tank and said hollow detector for delivering said liquid electrolyte from said supply tank to said hollow detector,
    a second conduit system connected to said hollow detector to remove liquid therein,
    a first electrode positioned in said hollow detector,
    a second electrode extending into said container outside said hollow detector so as to dip into the ultrapure water therein, and
    electrical means connected to said first and second electrodes to cause a current to flow therebetween through said ultrapure water in said container and the liquid in said hollow detector and to detect voltage pulses produced by impurities passing through said small hole in said hollow detector,
    the improvement wherein a deaeration device is connected to said first conduit system to deaerate the electrolyte passing through said first conduit system such that bubbles formed by electrolysis at said first and second electrodes will be redissolved, thus increasing the speed and sensitivity of measurement and reducing the current needed for measurement, said deaeration device comprising a chamber, a vacuum pump connected to said chamber and a tube extending through said chamber, said tube being connected into said first conduit system, said tube being made of a synthetic resin which is pervious to gases but not liquids.

2. The electrical pulse apparatus as defined in claim 1, wherein said synthetic resin is an ethylene tetrafluoride resin material.

3. The electrical pulse apparatus as defined in claim 1, wherein said synthetic resin is a silicone resin material.

* * * * *